(12) United States Patent
Sato et al.

(10) Patent No.: US 8,425,407 B2
(45) Date of Patent: Apr. 23, 2013

(54) ENDOSCOPE INSERTION PORTION

(75) Inventors: Eijiro Sato, Greenwich, CT (US); Eiji Matsuda, Hachioji (JP); Toru Shinmura, Hachioji (JP)

(73) Assignee: Olympus Medical Systems Corp. (JP)

( * ) Notice: Subject to any disclaimer, the term of this patent is extended or adjusted under 35 U.S.C. 154(b) by 766 days.

(21) Appl. No.: 12/556,733

(22) Filed: Sep. 10, 2009

(65) Prior Publication Data

US 2010/0069714 A1  Mar. 18, 2010

(30) Foreign Application Priority Data

Sep. 12, 2008 (JP) .................................. 2008-235270

(51) Int. Cl.
*A61B 1/04* (2006.01)
(52) U.S. Cl.
USPC ........... 600/130; 600/129; 600/141; 600/142; 600/153
(58) Field of Classification Search .......... 600/129–130, 600/141–142, 153
See application file for complete search history.

(56) References Cited

U.S. PATENT DOCUMENTS

| | | | | |
|---|---|---|---|---|
| 4,832,003 A | * | 5/1989 | Yabe | 600/109 |
| 5,002,041 A | * | 3/1991 | Chikama | 600/139 |
| 5,976,074 A | * | 11/1999 | Moriyama | 600/144 |
| 6,582,360 B1 | * | 6/2003 | Torii | 600/129 |
| 7,828,722 B2 | * | 11/2010 | Ooyatsu | 600/130 |
| 2001/0023313 A1 | * | 9/2001 | Ide | 600/142 |

FOREIGN PATENT DOCUMENTS

| | | |
|---|---|---|
| CN | 101069634 A | 11/2007 |
| EP | 1 854 398 | 11/2007 |
| JP | 3-66352 | 3/1991 |
| JP | 6-225851 | 8/1994 |
| JP | 8-299258 | 11/1996 |
| JP | 2836750 | 10/1998 |

OTHER PUBLICATIONS

European Search Report dated Nov. 18, 2009 in corresponding European Patent Application No. EP 09 01 1555 (English language).
Letter from German associate dated Nov. 19, 2009 forwarding the European Search Report dated Nov. 18, 2009 to Japanese associate, including discussion of relevancy thereof. German associate's letter dated Nov. 19, 2009 was date stamped received by Japanese associate on Nov. 25, 2009 (English language).
Chinese Office Action mailed Nov. 25, 2010 in connection with corresponding Chinese Patent Application No. 200910173156.9.

(Continued)

*Primary Examiner* — Matthew J Kasztejna
(74) *Attorney, Agent, or Firm* — Ostrolenk Faber LLP (57) ABSTRACT

An endoscope insertion portion includes an image pick-up assembly including an image pick-up unit and an image pick-up cable provided in order from the distal end portion to the proximal end side wherein the outer diameter of the image pick-up unit is larger than the outer diameter of the image pick-up cable, and a channel assembly arranged side by side with the image pick-up assembly and including a thin outer diameter portion and a thick outer diameter portion provided in order from the distal end portion to the proximal end side wherein a distal end portion of the thick outer diameter portion is arranged on more proximal end side than a proximal end portion of the image pick-up unit.

8 Claims, 5 Drawing Sheets

OTHER PUBLICATIONS

English translation of Chinese Office Action issued in connection with corresponding Chinese application provided as an explanation of prior art relevancy.

Japanese Office Action mailed Dec. 18, 2012 in connection with corresponding Japanese Patent Application No. 2008-235270 and English translation thereof.

* cited by examiner

ENDOSCOPE INSERTION PORTION

CROSS-REFERENCE TO RELATED APPLICATIONS

This application is based upon and claims the benefit of priority from prior Japanese Patent Application No. 2008-235270, filed Sep. 12, 2008, the entire contents of which are incorporated herein by reference.

BACKGROUND OF THE INVENTION

1. Field of the Invention

The present invention relates to an endoscope insertion portion, in particular, an endoscope insertion portion wherein an image pick-up assembly for picking up an observation image and a channel assembly used for an insertion of an accessory and the like are inserted through the endoscope insertion portion in the axial direction from the distal end portion to the proximal end side.

2. Description of the Related Art

In Jpn. Pat. Appln. KOKAI Publication No. 8-299258, an endoscope is disclosed. The endoscope includes an elongated insertion portion configured to be inserted into a cavity. A distal end rigid portion is formed on the distal end portion of the insertion portion. An image pick-up unit for picking up an observation image is provided in the distal end rigid portion. In the image pick-up unit, an objective optical system, an image pick-up device and an image pick-up board are provided in order from the distal end side to the proximal end side, and an image pick-up cable is extended from the proximal end portion of the image pick-up unit. The image pick-up unit and the image pick-up cable forms an image pick-up assembly. Moreover, a channel pipe is provided in the distal end rigid portion. The distal end portion of a channel tube is fitted onto and fixed to the proximal end side part of the channel pipe, and the channel tube is extended from the channel pipe. The channel pipe and the channel tube forms a channel assembly used for an insertion of an accessory and so on. The above image pick-up assembly and the channel assembly extend in the axial direction from the distal end portion to the proximal end side and arranged side by side in the endoscope insertion portion.

BRIEF SUMMARY OF THE INVENTION

In an aspect of the present invention, an endoscope insertion portion includes: an image pick-up assembly extending in an axial direction in the endoscope insertion portion, and including an image pick-up unit and an image pick-up cable provided in order from the distal end portion of the image pick-up assembly to the proximal end side of the image pick-up assembly wherein an outer diameter of the image pick-up unit is larger than an outer diameter of the image pick-up cable; and a channel assembly extending in the axial direction in the endoscope insertion portion, arranged side by side with the image pick-up assembly, and including a channel pipe and a channel tube provided in order from a distal end portion of the channel assembly to the proximal end side of the channel assembly wherein the channel pipe includes a pipe main portion formed by a distal end side part of the channel pipe, the channel tube includes a tube main portion formed by a proximal end side part of the channel tube, the channel assembly includes a thin outer diameter portion formed by at least the pipe main portion of the channel pipe, and a thick outer diameter portion formed by at least the tube main portion of the channel tube and including an outer diameter larger than an outer diameter of a thin outer diameter portion, and a distal end portion of the thick outer diameter portion is arranged on more proximal end side than a proximal end portion of the image pick-up unit.

In another aspect of the present invention, an endoscope includes an endoscope insertion portion, and the endoscope insertion portion includes: an image pick-up assembly extending in an axial direction in the endoscope insertion portion, and including an image pick-up unit and an image pick-up cable provided in order from the distal end portion of the image pick-up assembly to the proximal end side of the image pick-up assembly wherein an outer diameter of the image pick-up unit is larger than an outer diameter of the image pick-up cable; and a channel assembly extending in the axial direction in the endoscope insertion portion, arranged side by side with the image pick-up assembly, and including a channel pipe and a channel tube provided in order from a distal end portion of the channel assembly to the proximal end side of the channel assembly wherein the channel pipe includes a pipe main portion formed by a distal end side part of the channel pipe, the channel tube includes a tube main portion formed by a proximal end side part of the channel tube, the channel assembly includes a thin outer diameter portion formed by at least the pipe main portion of the channel pipe, and a thick outer diameter portion formed by at least the tube main portion of the channel tube and including an outer diameter larger than an outer diameter of a thin outer diameter portion, and a distal end portion of the thick outer diameter portion is arranged on more proximal end side than a proximal end portion of the image pick-up unit.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, one embodiment of the present invention will be explained referring to the drawings.

FIGS. 1 to 4 show the one embodiment of the present invention.

Figure 1:
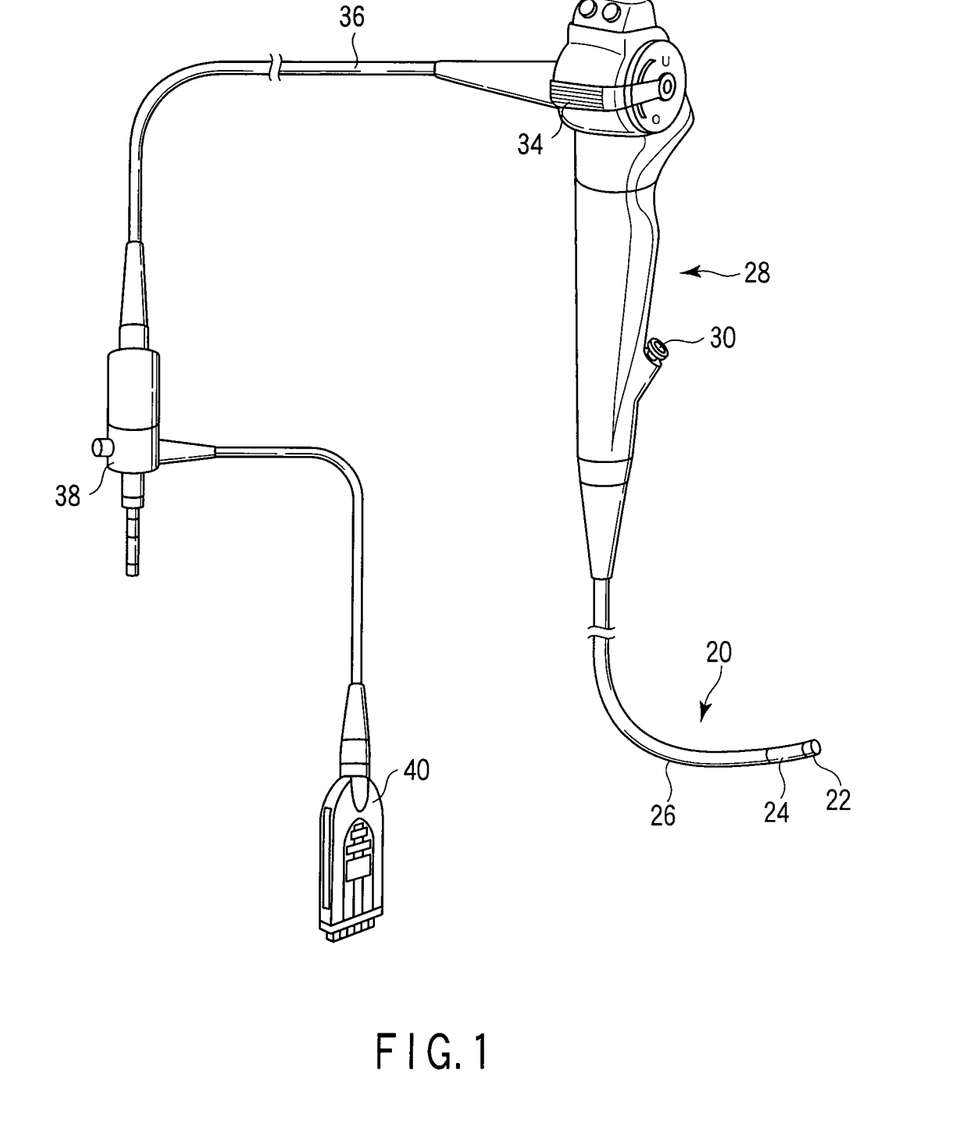
FIG. 1 is a perspective view showing an endoscope according to one embodiment of the present invention.
Figure 2:
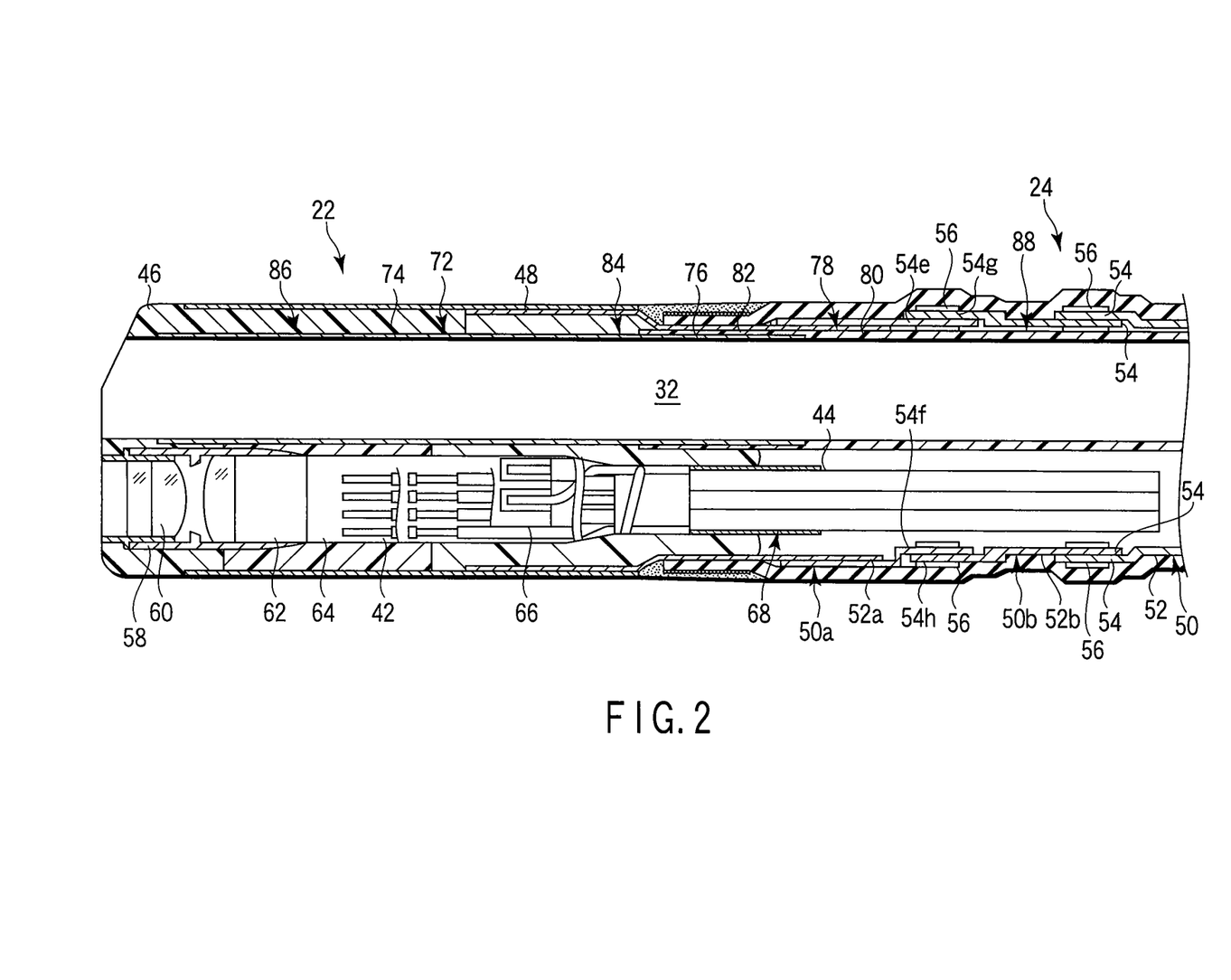
FIG. 2 is a longitudinal cross-sectional view showing an insertion portion according to the one embodiment of the present invention.

Referring to FIGS. 1 and 2, a schematic structure of an endoscope will be explained.

The endoscope includes an elongated insertion portion 20 configured to be inserted into a cavity in the body. In the insertion portion 20, a distal end rigid portion 22 as a distal end forming portion, a bending portion 24 configured to be actuated to be bent upward and downward, an insertion tube portion 26 being long and flexible are provided in order from the distal end side to the proximal end side. An operation portion 28 is coupled to the proximal end portion of the insertion portion 20 and configured to be held and operated by an operator. An accessory insertion inlet 30 is provided on the operation portion 28 and an accessory is adapted to be inserted into the accessory insertion inlet 30. An accessory channel 32 is extended from the accessory insertion inlet 30 to the distal end rigid portion 22 and the accessory is adapted to be inserted through the accessory channel 32. Moreover, a bending operation lever 34 is provided on the operation portion 28 and configured to operate the bending portion 24 to be bent. A universal cable 36 is extended from the operation portion 28, and a light source connecter 38 and an electrical connecter 40 are provided on the extended end portion of the universal cable 36. The light source connecter 38 and the electrical connecter 40 are configured to be connected to the light source apparatus and the video processor, respectively. Illumination light is to be generated in the light source apparatus, transmitted through a light guide extending between the light source connecter 38 and the distal end rigid portion 22, supplied to an illumination optical system in the distal end rigid portion 22, and emitted from the illumination optical system to an observation target. An observation image is to be picked up and then an image signal is to be generated by an image pick-up unit 42 in the distal end rigid portion 22, and the image signal is to be transmitted through the image pick-up cable 44 extending between the distal end rigid portion 22 and the electrical connecter 40, and output from the electrical connecter 40 to the video processor.

Figure 3:
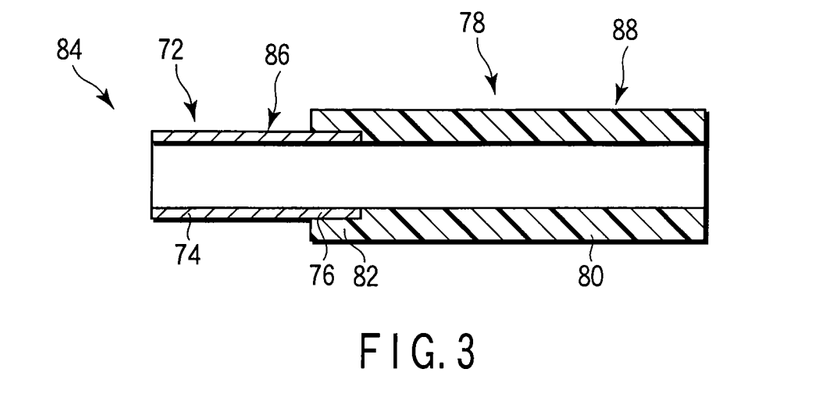
FIG. 3 is a schematic view showing a channel assembly according to the one embodiment of the present invention.
Figure 4:
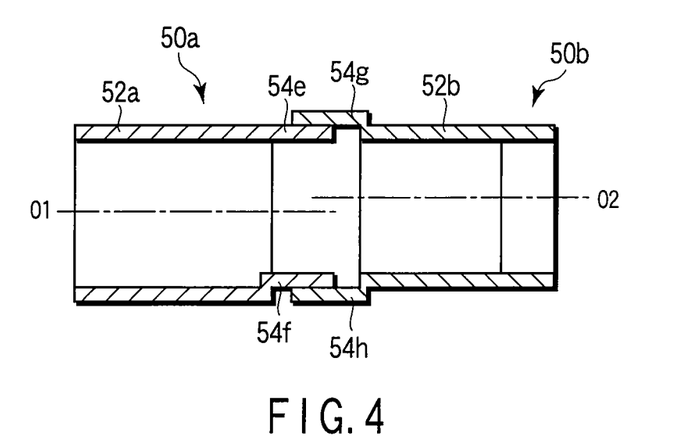
FIG. 4 is a schematic view showing a first and a second bending part according to the one embodiment of the present invention.

Referring to FIGS. 2 to 4, the distal end portion of the endoscope insertion portion 20 will be explained in detail.

Referring to FIG. 2, in the distal end rigid portion 22, a distal end member 46 and a coupling member 48 forming a framework of the distal end rigid portion 22 are provided in order from the distal end side to the proximal end side.

An observation bore 58 is formed in the axial direction in the distal end member 46. The distal end portion of the image pick-up unit 42 is fitted into the observation bore 58 from the proximal end side, and the distal end portion of the image pick-up unit 42 is fixed to the distal end member 46. An objective optical system 60, an image pick-up device 62, and an image pick-up board 64 are provided in order from the distal end side to the proximal end side in the image pick-up unit 42. Various kinds of signal lines 66 are extended from the image pick-up board 64, and put into an image pick-up cable 44 extending from the proximal end portion of the image pick-up unit 42. The image pick-up cable 44 extends from the distal end rigid portion 22 to the bending portion 24. The image pick-up unit 42 and the image pick-up cable 44 forms an image pick-up assembly 68, and the image pick-up assembly 68 extends in the axial direction from the distal end portion to the proximal end side in the insertion portion 20. In the image pick-up assembly 68, the outer diameter of the image pick-up unit 42 is larger than the outer diameter of the image pick-up cable 44. Moreover, the proximal end portion of the image pick-up unit 42 is arranged on more distal end side than the proximal end portion of the distal end rigid portion 22.

A channel bore 70 is formed in the axial direction in the distal end member 46. The distal end portion of a channel pipe 72 is fitted into the channel bore 70 from the proximal end side, and the channel pipe 72 is fixed to the distal end member 46. The channel pipe 72 is a thin and rigid member, and made of stainless steel, for example. The distal end portion of a channel tube 78 is coupled to the proximal end portion of the channel pipe 72. The channel tube 78 is a thick and soft member, and made of polytetrafluoroethylene, for example. The channel pipe 72 and the channel tube 78 forms a channel assembly 84, and the channel assembly 84 extends in the axial direction from the distal end portion to the proximal end side in the insertion portion 20.

Referring to FIGS. 2 and 3, in the embodiment, the channel pipe 72 is formed by the pipe main portion 74 on the distal end side part and the pipe fitting portion 76 on the proximal end portion. The outer diameter and the inner diameter of the channel pipe 72 is substantially fixed over the total axial length of the channel pipe 72. On the other hand, the channel tube 78 is formed by a tube fitting portion 82 on the distal end portion and a tube main portion 80 on the proximal end side part. The outer diameter of the channel tube 78 is substantially fixed over the total axial length, and larger than the outer diameter of the channel pipe 72. The inner diameter of the channel tube 78 is substantially equal to the outer diameter of the channel pipe 72 in the tube fitting portion 82, and substantially equal to the inner diameter of the channel pipe 72 in the tube main portion 80. Moreover, the axial length of the pipe fitting portion 76 of the channel pipe 72 is equal to the axial length of the tube fitting portion 82 of the channel tube 78. The pipe fitting portion 76 of the channel pipe 72 is fitted into and fixed to the tube fitting portion 82 of the channel tube 78. In the channel assembly 84, the pipe main portion 74 of the channel pipe 72 forms a thin outer diameter portion 86, and the whole channel tube 78 forms a thick outer diameter portion 88 whose outer diameter is larger than that of the thin outer diameter portion 86. Moreover, the distal end portion of the channel tube 78 of the channel assembly 84, that is, the distal end portion of the thick outer diameter portion 88 is arranged at the proximal end portion of the distal end rigid portion 22 and on more proximal end side than the proximal end portion of the image pick-up unit 42 of the image pick-up assembly 68.

Referring to FIG. 2 again, in the insertion portion 20, the image pick-up assembly 68 is arranged on the left side and the channel assembly 84 is arranged on the right side in the cross-section orthogonal to the axial direction of the insertion portion 20. That is, the left-light direction corresponds to an arrangement direction of the image pick-up assembly 68 and the channel assembly 84, and the up-down direction corresponds to an orthogonal direction orthogonal to the arrangement direction. As is mentioned above, regarding the image pick-up assembly 68, the proximal end portion of the image pick-up unit 42 is arranged on more distal end side than the proximal end portion of the distal end rigid portion 22. That is, the image pick-up unit 42 is arranged on the distal end side part of the distal end rigid portion 22, and the image pick-up cable 44 is arranged on the proximal end portion of the distal end rigid portion 22 and the bending portion 24. Moreover, regarding the channel assembly 84, the distal end portion of the channel tube 78 is arranged at the proximal end portion of the distal end rigid portion 22 and on more distal end side than the second bending part 50b. That is, the channel pipe 72 is arranged at the distal end rigid portion 22 and only the channel tube 78 is arranged on the bending portion 24.

In the bending portion 24, a large number of bending parts 50a, 50b, 50 is coupled in order in the axial direction so as to be rotatable upward and downward relative to each other. The bending part on the most distal end is referred to as a first bending part 50a, and the bending part which is second from the distal end is referred to as a second bending part 50b. In the first bending part 50a, the distal end side part of a cylindrical portion 52a is fitted onto and fixed to the proximal end side part of the coupling member 48 of the distal end rigid portion 22, and a pair of tongue portions 54e, 54f orthogonal to the left-right direction and symmetrical with each other about the central axis is protruded in the axial direction from the right and the left side on the distal end surface of the cylindrical portion 52a. In the bending part 50b, 50 which is second or over from the distal end, pairs of tongue portions 54g, 54h, 54 orthogonal to the left-right direction and symmetrical with each other about the central axis are protruded in the axial direction from the right and the left side on the distal and the proximal end surface of the cylindrical portion 52b, 52. In both the bending parts 50a, 50b, 50 adjacent to each other, the pair of tongue portions 54e, 54f, 54g, 54h, 54 on the proximal end side of the bending part 50a, 50b, 50 on the distal end side and the pair of tongue portions 54g, 54h, 54 on the distal end side of the bending part 50b, 50 on the proximal end side are overlapped with each other and coupled to each other so as to be rotatable upward and downward relative to each other by rivets 56.

In the bending part 50b, 50 which is second or more from the distal end, the both bending parts 50b, 50 adjacent to each other are coaxial with each other. That is, in each bending part 50b, 50, the pair of tongue portions 54 on the distal end side is arranged so as to be shifted outward in the left-right direction relative to the cylindrical portion 52, and the pair of tongue portions 54 on the proximal end side are aligned in the axial direction with the cylindrical portion 52b, 52. Moreover, in both the bending parts 50b, 50 adjacent to each other, the pair of tongue portions 54 on the distal end side of the bending part 50 on the proximal end side is overlapped with the radial outside of the pair of tongue portions 54 on the proximal end side of the bending part 50b, 50 on the distal end side. Such the position with respect to the left-right direction of the tongue portion 54 relative to the cylindrical portion 52b, 52 and the relative arrangement with respect to the left-right direction of both the tongue portions 54 overlapped with each other are referred to as a normal position and a normal arrangement.

Referring to FIGS. 2 and 4, the central axis of the second bending part 50b is arranged so as to be off-set to the right side, that is, from the side close to the image pick-up assembly 68 to the side close to the channel assembly 84 relative to the central axis of the first bending part 50a. That is, regarding the pair of tongue portions 54e, 54f in the first bending part 50a, the right side tongue portion 54e on the side close to the channel assembly 84 is in the normal position and aligned in the axial direction with the cylindrical portion 52a, and, in contrast, the left side tongue portion 54f on the side close to the image pick-up assembly 68 is in an off-set position different from the normal position, and not aligned in the axial direction with the first cylindrical portion 52a and arranged so as to be shifted rightward, that is, from the side close to the image pick-up assembly 68 to the side close to the channel assembly 84. The pair of tongue portions 54g, 54h on the distal end side of the second bending part 50b is in the normal position and arranged outside in the left-right direction relative to the second cylindrical portion 52b. The pair of tongue portions 54e, 54f of the first bending part 50a and the pair of tongue portions 54g, 54h on the distal end side of the second bending part 50b is in the normal arrangement, and the pair of tongue portions 54g, 54h on the distal end side of the second bending part 50b is overlapped with the outside in the left-right direction of the pair of tongue portions 54e, 54f of the first bending part 50a, respectively.

Therefore, the endoscope insertion portion 20 according to the embodiment exhibits the following effects.

In the endoscope insertion portion 20 according to the embodiment, the image pick-up unit 42 having the thick outer diameter is arranged on the distal end portion and the image pick-up cable 44 having the thin outer diameter is arranged on the proximal end side in the image pick-up assembly 68, and, in contrast, the thin outer diameter portion 86 is arranged on the distal end portion and the thick outer diameter portion 88 is arranged on the proximal end side in the channel assembly 84, and furthermore, the distal end portion of the thick outer diameter portion 88 is arranged on more proximal end side than the proximal end portion of the image pick-up unit 42. Therefore, when the channel assembly 84 is arranged as close to the image pick-up assembly 68 as possible and along the image pick-up assembly 68 in order to make the endoscope insertion portion 20 thinner, the image pick-up assembly 68 and the channel assembly 84 can be alternatively arranged in the axial direction and the channel assembly 84 can be arranged so as to be straight, and therefore, the channel tube 78 can be prevented from meandering.

Furthermore, the image pick-up unit 42 having the thick outer diameter and the thin outer diameter portion 86 are arranged side by side in the distal end rigid portion 22, and, in contrast, the image pick-up cable 44 having the thin outer diameter and the thick outer diameter portion 88 are arranged side by side in the second bending part 50b. Therefore, in the case where the central axis O2 of the second bending part 50b is coaxial with the central axis O1 of the distal end rigid portion 22 and the first bending part 50a, when the second bending part 24 is made thinner in order to make the endoscope insertion portion 20 thinner, the thick outer diameter portion 88 may meander close to the central axis and leftward, that is, from the side close to the channel assembly 84 to the side close to the image pick-up assembly 68 relative to the thin outer diameter portion 86. In the embodiment, the central axis O2 of the second bending part 50b is arranged so as to be shifted rightward, that is, from the side close to the image pick-up assembly 68 to the side close to the channel assembly 84 relative to the central axis O1 of the distal end rigid portion 22 and the first bending part 50a, and therefore, even when make the second bending part 50b thinner, the channel tube 78 can be arranged so as to be straight and it is possible to prevent the meander of the channel tube 78.

Moreover, a distance is referred to as an accessory minimum visible distance, which is a minimum protruding length of an accessory in which the accessory become observable by the image pick-up unit 42 when the accessory is protruded from the distal end rigid portion 22. In the embodiment, the channel assembly 84 can be arranged as close to the image pick-up assembly 68 as possible and the central axis of the channel pipe 72 can be arranged sufficiently close to the central axis of the image pick-up unit 42 without bringing about meander of the channel tube 78, and therefore, it is possible to make the accessory minimum visible distance small sufficiently.

It is noted that, although the tongue portion 54f is arranged so as to be off-set from the normal position in the first bending part 50a in the embodiment, the tongue portion 54g, 54h may be arranged so as to be off-set from the normal position in the second bending part 50b. For example, a pair of tongue portions 54e, 54f of a first bending part 50a is in a normal position and aligned in the axial direction with a cylindrical portion 52a. On the other hand, regarding a pair of tongue portions 54g, 54h on the distal end side of a second bending part 50b, a left side tongue portion 54h on the side close to an image pick-up assembly 68 is in a normal position and arranged so as to be shifted leftward relative to a cylindrical portion 52b, and, in contrast, a right side tongue portion 54g on the side close to a channel assembly 84 is in an off-set position different from a normal position, not arranged so as to be shifted rightward relative to the cylindrical portion 52b, and arranged so as to be aligned in the axial direction with the cylindrical portion 52b or shifted leftward, that is, from the side close to the channel assembly 84 to the side close to the image pick-up assembly 68. The pair of tongue portions 54e, 54f of the first bending part 50a and the pair of tongue portions 54g, 54h on the distal end side of the second cylindrical portion 52b forms a normal arrangement and the pair of tongue portions 54g, 54h on the distal end side of the second cylindrical portion 52b is overlapped with the outside with respect to the left-right direction of the pair of tongue portions 54e, 54f of the first bending part 50a, respectively.

Figure 5:
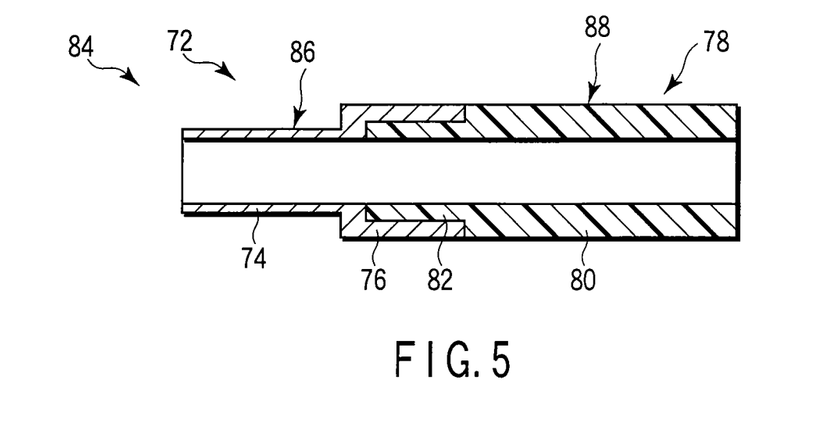
FIG. 5 is a schematic view showing a channel assembly according to a first modified example of the one embodiment of the present invention.

FIG. 5 shows a first modified example of the one embodiment of the present invention.

In the modified example, a structure of fitting parts of a channel pipe 72 and a channel tube 78 is different from that of the first embodiment. That is, the outer diameter of a pipe fitting portion 76 is larger than the outer diameter of a pipe main portion 74 in the channel pipe 72. The inner diameter of the distal end side part of the pipe fitting portion 76 is equal to the inner diameter of the pipe main portion 74, and the inner diameter of the proximal end side part of the pipe fitting portion 76 is larger than the inner diameter of the pipe main portion 74 and the distal end side part of the pipe fitting portion 76. On the other hand, in the channel tube 78, the inner diameter of the channel tube 78 is fixed along the axial direction, and equal to the inner diameter of the pipe main portion 74 of the channel pipe 72 and the distal end side part of the pipe fitting portion 76. The outer diameter of the tube fitting portion 82 is equal to the inner diameter of the pipe fitting portion 76, and the outer diameter of a tube main portion 80 is larger than the outer diameter of the tube fitting portion 82, and equal to the outer diameter of the pipe fitting portion 76 of the channel pipe 72. Moreover, the axial length of the proximal end side part of the pipe fitting portion 76 is equal to the axial length of the tube fitting portion 82. Moreover, the tube fitting portion 82 is fitted into and fixed to the pipe fitting portion 76. In the channel assembly 84, the pipe main portion 74 of the channel pipe 72 forms a thin outer diameter portion 86, and the pipe fitting portion 76 of the channel pipe 72 and the tube main portion 80 of the channel tube 78 forms a thick outer diameter portion 88.

Figure 6:
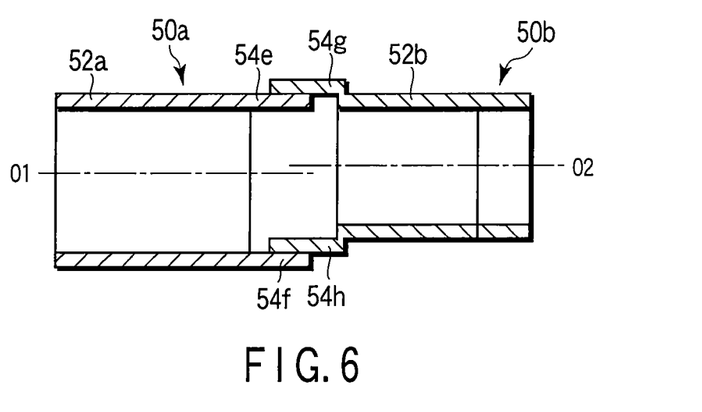
FIG. 6 is a schematic view showing a first and a second bending part according to a second modified example of the one embodiment of the present invention.

FIG. 6 shows a second modified example of the one embodiment of the present invention.

In the modified example, an off-set structure of a second bending part 50b is different from that of the first embodiment. That is, a pair of tongue portions 54e, 54f of a first bending part 50a is in a normal position, and aligned in the axial direction with a first cylindrical portion 52a, and also, a pair of tongue portions 54g, 54h on the distal end side of the second bending part 50b is in a normal position, and arranged so as to be shifted outward in the left-right direction relative to a second cylindrical portion 52b. A right side tongue portion 54e on the side close to the channel assembly 84 of the first bending part 50a and the right side tongue portion 54g on the distal end side of the second bending part 50b forms a normal arrangement and so a right side tongue portion 54g on the distal end side of the second bending part 50b is overlapped with the outside in the left-right direction of the right side tongue portion 54e of the first bending part 50a. In contrast, a left side tongue portion 54f on the side close to the image pick-up assembly 68 of the first bending part 50a and a left side tongue portion 54h on the distal end side of the second bending part 50b form an off-set arrangement different from a normal arrangement and so the left side tongue portion 54h on the distal end side of the second bending part 50b is overlapped with the inside with the left-right direction of the left side tongue portion 54f of the first bending part 50a.

Figure 7:
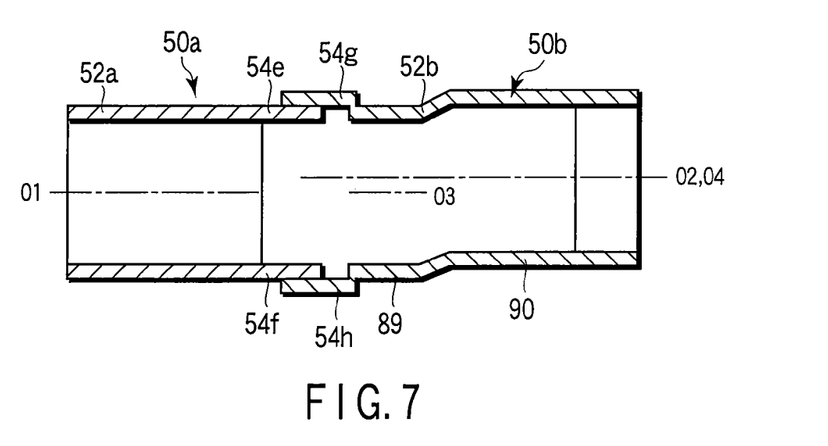
FIG. 7 is a schematic view showing a first and a second bending part according to a third modified example of the one embodiment of the present invention.

FIG. 7 shows a third modified example of the one embodiment of the present invention.

In the modified example, an off-set structure of a second bending part 50b is different from those of the one embodiment and a second modified example. That is, a normal position and a normal arrangement are used in a first and a second bending part 50a, 50b. However, in a cylindrical portion 52b of the second bending part 50b, a coaxial portion 89 and an off-set portion 90 are provided in order from the distal end side to the proximal end side. The axial length of the coaxial portion 89 is sufficiently short and the axial length of the off-set portion 90 is sufficiently large in comparison with the axial length of the coaxial portion 89, and the off-set portion 90 forms the central axis O2 of the second bending part 50b. The central axis O1 of the first bending part 50a and the central axis O3 of the coaxial portion 89 of the second bending part 50b are coaxial with each other. On the other hand, in the second bending part 50b, the central axis O4 of the off-set portion 90 is arranged so as to be off-set rightward, that is, from the side close to an image pick-up assembly 68 to the side close to a channel assembly 84 relative to the central axis O3 of the coaxial portion 89 in the cross-section orthogonal to the axial direction.

Figure 8:
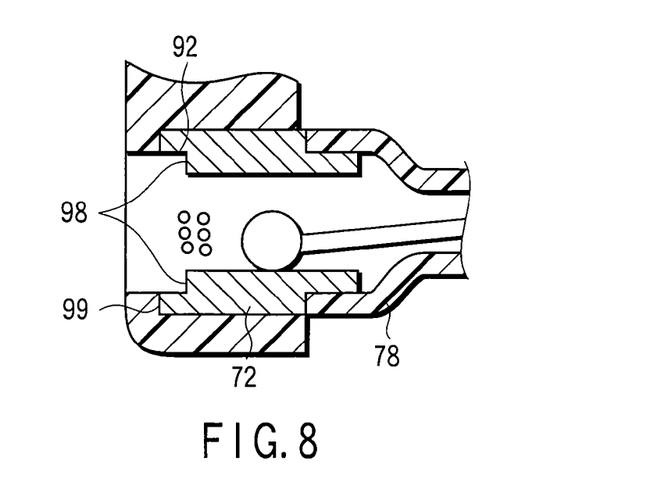
FIG. 8 is a longitudinal cross-sectional view showing the distal end portion of an endoscope according to a first referential embodiment of the present invention.
Figure 9:
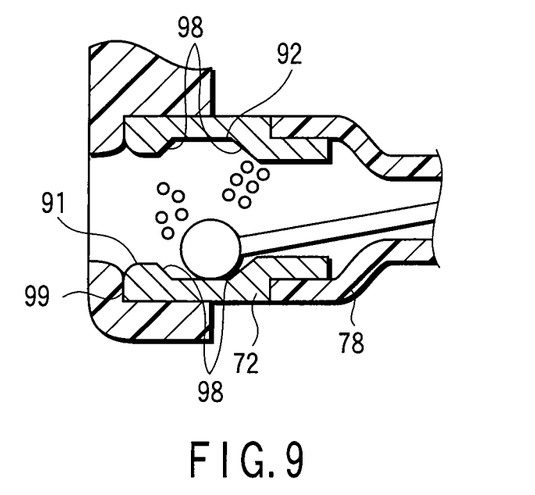
FIG. 9 is a longitudinal cross-sectional view showing the distal end portion of an endoscope according to a second referential embodiment of the present invention.
Figure 10:
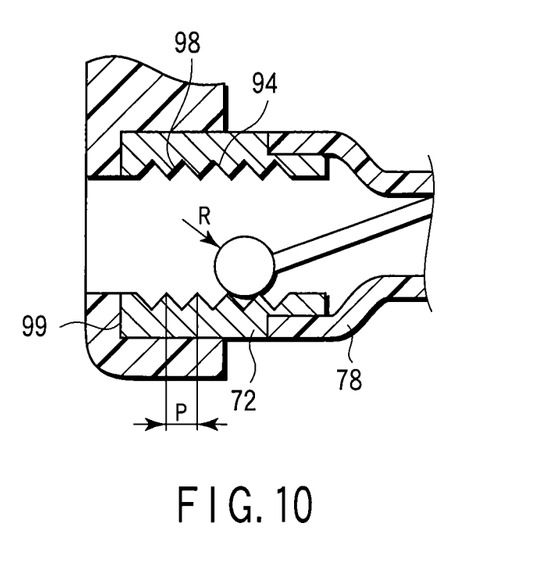
FIG. 10 is a longitudinal cross-sectional view showing the distal end portion of an endoscope according to a third referential embodiment of the present invention.

FIGS. 8 to 10 show each of referential embodiments of the present invention.

In an endoscope used together with a high-frequency accessory, in order to prevent a high-frequency current from flowing into the endoscope from the high-frequency accessory inserted through an accessory channel to generate noise and the like in an image pick-up unit, a metal channel pipe is held only a insulating member and insulated from other conducting members. Here, in particular, when the distal end portion of the endoscope is dipped into an electrolyte solution such as a saline, a high-frequency current flowing into the channel pipe from the high-frequency accessory then flow into an electrolyte solution, heating and discharging may be generated on the edge of the end portion of the channel pipe, and a bonding argent fixing the channel pipe, a resin member and so on may be damaged.

The referential embodiment has been made in the view of the above mentioned problem and aimed at providing an endoscope insertion portion wherein a bonding argent fixing the channel pipe, a resin member and others are prevented from being damaged.

FIG. 8 shows a first referential embodiment of the present invention.

In the referential embodiment, a concave portion 92 is formed on the axial distal end portion of the inner peripheral portion of a channel pipe 72 over the whole periphery, and a step portion 98 is formed on the inner peripheral portion of the channel pipe 72. In the channel pipe 72 of the referential embodiment, heating and discharging is generated on the edge of the step portion 98 on the inner peripheral surface side of the channel pipe 72 and heating and discharging is suppressed on the edge of the end portion 99, and therefore, a bonding agent fixing the channel pipe 72, a resin member and so on are prevented from being damaged.

FIG. 9 shows a second referential embodiment of the present invention.

In the referential embodiment, a concave portion 92 is formed on the axial middle part of the inner peripheral portion of a channel pipe 72 over the whole periphery, and a step portion 98 is formed on the inner peripheral portion of the channel pipe 72. Furthermore, the edge of the end portion 99 of the channel pipe 72 is shaped into a smooth R-shape 91. In the channel pipe 72 of the referential embodiment, heating and discharging is generated on the edge of the step portion 98 of the inner peripheral surface side of the channel pipe 72, and also, the edge of the end portion 99 has the smooth R-shape 91, and therefore, heating and discharging is suppressed on the edge of the end portion 99.

FIG. 10 shows a third referential embodiment of the present invention.

In a high-frequency accessory used together with an endoscope according to the referential embodiment, a treatment portion 96 which is spherical, for example, is formed on the distal end portion, and the treatment portion 96 has a certain radius R. Moreover, an internal thread portion 94 is formed on the inner peripheral portion of a channel pipe 72, and a step portion 98 is formed by the internal thread portion 94. The pitch P of the internal thread portion 94 is smaller than the radius R of the treatment portion 96 of the high-frequency accessory. In the channel pipe 72 of the referential embodiment, heating and discharging is generated on the edge of the internal thread portion 94 on the inner peripheral surface side of the channel pipe 72, and therefore, heating and discharging is suppressed on the edge of the end portion 99, and also, the pitch P of the internal thread portion 94 is smaller than the radius R of the treatment portion 96 of the high-frequency accessory, and therefore, the treatment portion 96 is prevented from being engaged on the step portion 98 of the internal thread portion 94.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope insertion portion comprising:
an image pick-up assembly extending in an axial direction in the endoscope insertion portion, and the image pick-up assembly including:
an image pick-up unit and
an image pick-up cable extending from a proximal end of the image pick-up unit to the proximal end of the insertion portion
wherein an outer diameter of the image pick-up unit is larger than an outer diameter of the image pick-up cable; and
a channel assembly extending in the axial direction in the endoscope insertion portion, arranged side by side with the image pick-up assembly, and including:
a channel pipe which includes a thin outer diameter portion and
a channel tube which includes a thick outer diameter portion including an outer diameter larger than an outer diameter of the thin outer diameter portion and which is provided to the proximal end of the channel pipe,
wherein a distal end portion of the thick outer diameter portion of the channel tube is arranged on a more proximal end side than a proximal end portion of the image pick-up unit; and
wherein the endoscope insertion portion includes a distal end forming portion and a bending portion provided in order from the distal end portion of the endoscope insertion portion to the proximal end portion of the endoscope insertion portion,
the bending portion includes a plurality of cylindrical bending parts coupled to each other in the axial direction so as to be rotatable relative to each other and including a first bending part on the most distal end coaxially coupled to the distal end forming portion and a second bending part coupled to the proximal end side of the first bending part, and
a central axis of the second bending part is arranged so as to be off-set from a side close to the image sick-us assembly to a side close to the channel assembly relative to a central axis of the first bending part in a cross-section orthogonal to the axial direction of the endoscope insertion portion.

2. The endoscope insertion portion according to claim 1, wherein the channel pipe includes a pipe fitting portion formed on a proximal end portion of the channel pipe and an outer diameter and an inner diameter of the channel pipe are substantially fixed along an axial direction of the channel pipe,
the channel tube includes a tube fitting portion and a tube main portion, the tube fitting portion formed on a distal end portion of the channel tube, an outer diameter of the channel tube is substantially fixed along an axial direction of the channel tube and larger than the outer diameter of the channel pipe, an inner diameter of the tube fitting portion is substantially equal to the outer diameter of the channel pipe, an inner diameter of the tube main portion is substantially equal to the inner diameter of the channel pipe, and an axial length of the tube fitting portion is substantially equal to an axial length of the pipe fitting portion,
the pipe fitting portion is fitted into and fixed to the tube fitting portion.

3. The endoscope insertion portion according to claim 1, wherein the channel pipe includes a pipe fitting portion formed by the proximal end portion of the channel pipe, an outer diameter of the pipe fitting portion is larger than an outer diameter of the pipe main portion, an inner diameter of a distal end side part of the pipe fitting portion is substantially equal to an inner diameter of the pipe main portion, and an inner diameter of a proximal end side part of the pipe fitting portion is larger than the inner diameter of the distal end side part of the pipe fitting portion,
the channel tube includes a tube fitting portion formed on a distal end portion of the channel tube, an outer diameter of the tube fitting portion is substantially equal to the inner diameter of the proximal end side part of the pipe fitting portion, an outer diameter of the tube main portion is larger than the outer diameter of the tube fitting portion and substantially equal to the outer diameter of the pipe fitting portion, the inner diameter of the channel tube is substantially fixed along an axial direction of the channel tube and substantially equal to the inner diameter of the distal end side part of the pipe fitting portion, and an axial length of the tube fitting portion is substantially equal to an axial length of the proximal end side part of the pipe fitting portion, and the pipe fitting portion is fitted onto and fixed to the tube fitting portion, and the thin outer diameter portion is formed by the pipe main portion, and the thick outer diameter portion is formed by the pipe fitting portion and the tube main portion.

4. The endoscope insertion portion according to claim 1, wherein the first bending part includes a first cylindrical portion and a first tongue portion provided on at least one side in an arrangement direction of the image pick-up assembly and the channel assembly on a proximal end side end surface portion of the first cylindrical portion and protruded in the axial direction, the second bending part includes a second cylindrical portion and a second tongue portion provided on at least the one side in the arrangement direction on a distal end side end surface portion of the second cylindrical portion and protruded in the axial direction, the first tongue portion and the second tongue portion are overlapped with each other in the arrangement direction and coupled to each other so as to be rotatable relative to each other in an orthogonal direction orthogonal to the arrangement direction, and a position with respect to the arrangement direction of the first tongue portion relative to the first cylindrical portion in the first bending part or a position with respect to the arrangement direction of the second tongue portion relative to the second cylindrical portion in the second bending part forms an off-set position wherein a central axis of the second bending part is arranged so as to be off-set from a side close to the image pick-up assembly to a side close to the channel assembly relative to a central axis of the first bending part.

5. The endoscope insertion portion according to claim 1, wherein the first bending part includes a first cylindrical portion and a first tongue portion provided on at least one side in the arrangement direction of the image pick-up assembly and the channel assembly on a proximal end side end surface portion of the first cylindrical portion and protruded in the axial direction, the second bending part includes a second cylindrical portion and a second tongue portion provided on at least the one side in the arrangement direction on a distal end side end surface portion of the second cylindrical portion and protruded in the axial direction, the first tongue portion and the second tongue portion are overlapped with each other in the arrangement direction and coupled to each other so as to be rotatable relative to each other in an orthogonal direction orthogonal to the arrangement direction, and a relative arrangement with respect to the arrangement direction of both the tongue portions overlapped with each other forms an off-set arrangement wherein a central axis of the second bending part is arranged so as to be off-set from a side close to the image pick-up assembly to a side close to the channel assembly relative to a central axis of the first bending part.

6. The endoscope insertion portion according to claim 1, wherein the second bending part includes a cylindrical portion, the cylindrical portion includes a coaxial portion formed by a distal end side part of the cylindrical portion and an off-set portion formed by a proximal end side part of the cylindrical portion, and a central axis of the coaxial portion is coaxial with a central axis of the first bending part, and a central axis of the off-set portion is arranged so as to be off-set from a side close to the image pick-up assembly to a side close to the channel assembly relative to a central axis of the coaxial portion and forms a central axis of the second bending part in a cross-section orthogonal to the axial direction of the endoscope insertion portion.

7. An endoscope comprising the endoscope insertion portion according to claim 1.

8. The endoscope insertion portion according to claim 1, wherein the image pick-up unit includes an objective optical system, an image pick-up device and an image pick-up board from a distal end portion to a proximal end portion of the endoscope insertion portion in sequence, the image pick-up cable extends from a proximal end of the image pick-up board to the proximal end of the insertion portion, and the distal end portion of the thick outer diameter portion is arranged on a more proximal end side than a proximal end portion of the image pick-up board.

* * * * *